(12) United States Patent
Glaeser et al.

(10) Patent No.: US 11,484,575 B2
(45) Date of Patent: Nov. 1, 2022

(54) COMPOSITIONS AND METHODS COMPRISING BONE MORPHOGENETIC PROTEIN AND NEMO BINDING PEPTIDE

(71) Applicants: Cedars-Sinai Medical Center, Los Angeles, CA (US); Warsaw Orthopedic, Inc., Warsaw, IN (US)

(72) Inventors: Juliane Glaeser, Los Angeles, CA (US); Hyun Bae, Los Angeles, CA (US); Linda Kanim, Los Angeles, CA (US); Dmitriy Sheyn, Los Angeles, CA (US); Khosrowdad Salehi, Los Angeles, CA (US)

(73) Assignees: Cedars-Sinai Medical Center, Los Angeles, CA (US); Warsaw Orthopedic, Inc., Warsaw, IN (US)

( * ) Notice: Subject to any disclaimer, the term of this patent is extended or adjusted under 35 U.S.C. 154(b) by 83 days.

(21) Appl. No.: 16/721,831

(22) Filed: Dec. 19, 2019

(65) Prior Publication Data
US 2020/0206315 A1     Jul. 2, 2020

Related U.S. Application Data

(60) Provisional application No. 62/785,921, filed on Dec. 28, 2018.

(51) Int. Cl.
| | |
|---|---|
| *A61K 38/18* | (2006.01) |
| *A61K 38/08* | (2019.01) |
| *A61K 38/17* | (2006.01) |
| *A61P 29/00* | (2006.01) |
| *A61K 9/00* | (2006.01) |
| *A61K 47/42* | (2017.01) |

(52) U.S. Cl.
CPC ........ *A61K 38/1875* (2013.01); *A61K 9/0085* (2013.01); *A61K 38/08* (2013.01); *A61K 38/1709* (2013.01); *A61K 47/42* (2013.01); *A61P 29/00* (2018.01)

(58) Field of Classification Search
CPC .............. A61K 38/1875; A61K 38/014; A61K 9/0085; A61K 38/08
See application file for complete search history.

(56) References Cited

U.S. PATENT DOCUMENTS 9,717,779 B2 * 8/2017 King ...................... A61L 27/24

OTHER PUBLICATIONS

Huang et al. "Opposing TNF-a/IL-1b- and BMP-2-activated MAPK signaling pathways converge on Runx2 to regulate BMP-2-induced osteoblastic differentiation", Cell Death and Disease, 2014, pp. 1-11 (Year: 2014).*
Gleeson et al., "Addition of Hydroxyapatite Improves Stiffness, Interconnectivity and Osteogenic Potential of a Highly Porous Collagen-Based Scaffold for Bone Tissue Regeneration", European Cells and Materials, 2010, pp. 218-230 (Year: 2010).*
Huang et al. "Opposing TNF-/IL-1- and BMP-2-activated MAPK signaling pathways converge on Runx2 to regulate BMP-2-induced osteoblastic differentiation", Cell Death and Disease, 2014, pp. 1-11 (Year: 2014).*
Li et al. "NEMO-binding domain peptide promotes osteoblast differentiation impaired by tumor necrosis factor alpha", Biochemical and Biophysical Research Communications, 2010, pp. 1228-1233 (Year: 2010).*
Glaeser et al. "Anti-Inflammatory Peptide Attenuates Edema and Promotes BMP-2 Induced Bone Formation in Spine Fusion", Tissue Engineering Part A, EPUB Jul. 3, 2018, 1641-1651 (Year: 2018).*

* cited by examiner

*Primary Examiner* — Lianko G Garyu
(74) *Attorney, Agent, or Firm* — Sorell, Lenna & Schmidt, LLP; William D. Schmidt, Esq.

(57) ABSTRACT

An osteogenic composition for implantation at or near a target tissue site beneath the skin is provided, the osteogenic composition comprising bone morphogenetic protein and a NEMO binding domain peptide, where the NEMO binding domain peptide reduces soft tissue inflammation at or near the target tissue site. In some embodiments, a method is provided for treating a target tissue site in a patient in need of such treatment, the method comprising implanting an osteogenic composition comprising bone morphogenetic protein and a NEMO binding domain peptide, where the NEMO binding domain peptide reduces soft tissue inflammation at or near the target tissue site.

8 Claims, 3 Drawing Sheets
Specification includes a Sequence Listing.

Fig. 3

COMPOSITIONS AND METHODS COMPRISING BONE MORPHOGENETIC PROTEIN AND NEMO BINDING PEPTIDE

CROSS-REFERENCE TO RELATED APPLICATION

This application claims the benefit of and priority to U.S. Provisional Patent Application No. 62/785,921 filed Dec. 28, 2018, the entire disclosure of which is incorporated by reference herein.

Sequence Listing

The entire contents of a Sequence Listing titled "SequenceListing.txt" created on Sep. 23, 2021 and having a size of one kilobyte, which has been submitted in electronic form in connection with the present application, is hereby incorporated by reference herein in its entirety.

BACKGROUND

Bone defects may be caused by a number of different factors including, but not limited to, trauma, pathological disease or surgical intervention. Because bone provides both stability and protection to an organism, these defects can be problematic. In order to address these defects, compositions and carriers that contain both natural and synthetic materials have been developed. These compositions and carriers may, depending upon the materials contained within them, be used to repair tissues and to impart desirable biological and/or mechanical properties to the bone defect.

Compositions and carriers may contain materials that are found in mammalian bone tissue which contains one or more proteinaceous materials, active during growth and natural bone healing that can induce a developmental cascade of cellular events resulting in bone formation. Various developmental factors are present in bone. These include bone morphogenetic proteins (BMPs), other bone inductive proteins, bone growth factors, or osteogenic proteins.

BMPs are a class of proteins in the superfamily of transforming growth factor-beta (TGF-β) thought to have osteoinductive or growth-promoting activities on endogenous bone tissue, or function as pro-collagen precursors. Because of these qualities, BMP has been commonly used in conjunction with compositions and carriers (e.g., bone scaffolds and matrices) for bone formation at bone defect sites and bone void sites. For example, bone morphogenetic protein 2 (BMP-2) is commonly placed on a collagen carrier and implanted at a target tissue site. Once the collagen carrier is implanted, it becomes a stationary matrix and the BMP-2 would draw osteoblasts and osteoclasts into the matrix in order to form new bone for fusion. The matrix containing the BMP-2 will promote the migration, proliferation and differentiation of bone cells for bone regeneration. Sometimes, BMP-2 may induce soft tissue edema, where there is inflammation and swelling at the implantation site.

The nuclear factor kB (NFκB) is an essential modulator-binding domain (NEMO binding domain or NBD) and blocks the activation of the IkB kinase (IKK) complex. NFκB is a central regulator of immune response through regulation of genes encoding pro-inflammatory cytokines, such as TNF-α and Il-1β. NEMO binding domain peptide (NBD) is a non-toxic agent that allows for the selective inhibition of NFκB activation without affecting NFκB's basal activity.

There is a need to develop new compositions and methods to reduce or prevent BMP-2 induced soft tissue edema.

SUMMARY

Compositions and methods are provided that reduce or prevent BMP-2 induced soft tissue edema. In some embodiments, there is an osteogenic composition for implantation at or near a target tissue site beneath the skin, the osteogenic composition comprising bone morphogenetic protein and a NEMO binding domain peptide, wherein the NEMO binding domain peptide reduces soft tissue inflammation at or near the target tissue site.

In some embodiments, there is an osteogenic composition for implantation at or near a target tissue site beneath the skin, the osteogenic composition comprising bone morphogenetic protein-2, a NEMO binding domain peptide, and a biodegradable matrix comprising a porous collagen surface, wherein the NEMO binding domain peptide reduces soft tissue inflammation at or near the target tissue site.

In some embodiments, there is a method for treating a target tissue site in a patient in need of such treatment, the method comprising implanting an osteogenic composition at or near the target tissue site beneath the skin, the osteogenic composition comprising bone morphogenetic protein-2, a NEMO binding domain peptide, and a biodegradable matrix comprising a porous collagen surface, wherein the NEMO binding domain peptide reduces soft tissue inflammation at or near the target tissue.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent regarding the following description, appended claims and accompanying drawings.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of promoting an understanding of the principles of the disclosure, reference will now be made to certain embodiments and specific language will be used to describe the same. It will nevertheless be understood that no limitation of the scope of the disclosure is thereby intended, such alterations and further modifications in the illustrated device, and such further applications of the principles of the disclosure as described herein being contemplated as would normally occur to one skilled in the art to which the disclosure relates.

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present application. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations; the numerical representations are as precise as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Additionally, unless defined otherwise or apparent from context, all technical and scientific terms used herein have the same meanings as commonly understood by one of ordinary skill in the art to which this disclosure belongs.

Unless explicitly stated or apparent from context, the following terms are phrases have the definitions provided below:

Definitions

It is noted that, as used in this specification and the appended claims, the singular forms "a," "an," and "the," include plural referents unless expressly and unequivocally limited to one referent. Thus, for example, reference to "a dose" includes one, two, three or more doses.

The term "patient" refers to a biological system to which a treatment can be administered. A biological system can include, for example, an individual cell, a set of cells (e.g., a cell culture), an organ, or a tissue. Additionally, the term "patient" can refer to animals, including, without limitation, humans.

The term "mammal" refers to organisms from the taxonomy class "mammalian," including but not limited to humans, other primates such as chimpanzees, apes, orangutans and monkeys, rats, mice, cats, dogs, cows, horses, etc.

The term "target tissue site" is intended to mean the location of the tissue to be treated. Typically the placement site of the matrix will be the same as the target site to provide for optimal targeted drug delivery. However, the present application also contemplates positioning the matrix at a placement site at or near the target site such that the therapeutic agent can be delivered to the surrounding vasculature, which carries the agent to the desired nearby target site. As used herein, the term "at or near" includes embodiments where the placement site and target site are within close proximity.

A "therapeutically effective amount" or "effective amount" is such that when administered, the drug (e.g., BMP-2, NEMO or NBD) results in alteration of the biological activity, such as, for example, promotion of bone, cartilage and/or other tissue, and/or reduction or alleviation of pain, and/or inflammation. The dosage administered to a patient can be as single or multiple doses depending upon a variety of factors, including the drug's administered pharmacokinetic properties, the route of administration, patient conditions and characteristics (sex, age, body weight, health, size, etc.), extent of symptoms, concurrent treatments, frequency of treatment and the effect desired.

The terms "treating" and "treatment" when used in connection with a disease or condition refer to executing a protocol that may include a bone repair procedure, where the bone implant and/or one or more drugs are administered to a patient (human, other normal or otherwise or other mammal), in an effort to alleviate signs or symptoms of the disease or condition or immunological response and/or inflammation. Alleviation can occur prior to signs or symptoms of the disease or condition appearing, as well as after their appearance. Thus, treating or treatment includes preventing or prevention of disease or undesirable condition. In addition, treating, treatment, preventing or prevention do not require complete alleviation of signs or symptoms, does not require a cure, and specifically includes protocols that have only a marginal effect on the patient.

The term "bone," as used herein, refers to bone that is cortical, cancellous or cortico-cancellous of autogenous, allogeneic, xenogeneic, or transgenic origin.

"NBD" or "NEMO Binding Domain" refers the nuclear factor NFκB essential modulator-binding domain peptide and/or its sequence. In some embodiments, an 11 amino acid sequence was identified within IKK comprising the binding domain between IKK beta and IKK gamma. This peptide, known as the NEMO binding domain (NBD) is able to block the interaction of IKK alpha and beta (two catalytic subunits of NF-kappa B activation) with the regulatory subunit IKK gamma (NEMO). When this short peptide sequence TALDWSWLQTE (SEQ ID NO: 1) (NBD) was linked to a protein transduction domain, it can lead to a dose dependent inhibition of NF-kappa B signaling in tissue culture and in animal models. NBD is described in US Publication Nos. 2018/0169078 and 2015/0031598, the entire disclosures of which are incorporated herein by reference.

In some embodiments, NBD includes short peptide sequence TALDWSWLQTE (SEQ ID NO: 1) either with or without a terminal glutamine residue. The NBD sequence can include truncations, amino acid deletions, and/or amino acid modifications of NBD.

The "matrix" of the present application is utilized as a scaffold for bone and/or cartilage repair, regeneration, and/or augmentation. Typically, the matrix provides a 3-D matrix of interconnecting pores, which acts as a pliant scaffold for cell migration. The morphology of the matrix guides cell migration and cells are able to migrate into or over the matrix, respectively. The cells then are able to proliferate and synthesize new tissue and form bone and/or cartilage.

The phrase "osteogenic composition" refers to a composition that comprises a substance that promotes bone growth. In some embodiments, osteogenic compositions as described herein can be delivered to other surgical sites, particularly sites at which bone growth is desired. These include, for instance, the repair of spine (e.g., vertebrae fusion) cranial defects, iliac crest back-filling, acetabular defects, in the repair of tibial plateau, long bone defects, spinal site defects or the like. Such methods can be used to treat major or minor defects in these or other bones caused by trauma (including open and closed fractures), disease, or congenital defects, for example.

Matrix

The matrix provides a tissue scaffold for the cells to guide the process of tissue formation in vivo in three dimensions. The morphology of the matrix guides cell migration and cells are able to migrate into or over the scaffold. The cells then are able to proliferate and synthesize new tissue and form bone and/or cartilage. In some embodiments, one or more tissue matrices are stacked on one another.

In some embodiments, the matrix comprises a plurality of pores. In some embodiments, at least 10% of the pores are between about 10 micrometers and about 500 micrometers at their widest points. In some embodiments, at least 20% of the pores are between about 50 micrometers and about 150 micrometers at their widest points. In some embodiments, at least 30% of the pores are between about 30 micrometers and about 70 micrometers at their widest points. In some embodiments, at least 50% of the pores are between about 10 micrometers and about 500 micrometers at their widest points. In some embodiments, at least 90% of the pores are between about 50 micrometers and about 150 micrometers at their widest points. In some embodiments, at least 95% of the pores are between about 100 micrometers and about 250 micrometers at their widest points. In some embodiments, 100% of the pores are between about 10 micrometers and about 300 micrometers at their widest points.

In some embodiments, the matrix has a porosity of at least about 30%, at least about 50%, at least about 60%, at least about 70%, at least about 90%. The pore may support ingrowth of cells, formation or remodeling of bone, cartilage and/or vascular tissue.

The matrix may comprise natural and/or synthetic material. For example, the tissue scaffold may comprise poly (alpha-hydroxy acids), poly (lactide-co-glycolide) (PLGA), polylactide (PLA), polyglycolide (PG), polyethylene glycol (PEG) conjugates of poly (alpha-hydroxy acids), polyorthoesters (POE), polyaspirins, polyphosphagenes, collagen, hydrolyzed collagen, gelatin, hydrolyzed gelatin, fractions of hydrolyzed gelatin, elastin, starch, pre-gelatinized starch, hyaluronic acid, chitosan, alginate, albumin, fibrin, vitamin E analogs, such as alpha tocopheryl acetate, d-alpha tocopheryl succinate, D,L-lactide, or L-lactide, -caprolactone, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAM (sucrose acetate isobutyrate), polydioxanone, methylmethacrylate (MMA), MMA and N-vinylpyyrolidone, polyamide, oxycellulose, copolymer of glycolic acid and trimethylene carbonate, polyesteramides, polyetheretherketone, polymethylmethacrylate, silicone, hyaluronic acid, chitosan, or combinations thereof.

In some embodiments, the matrix may comprise a resorbable ceramic (e.g., hydroxyapatite, tricalcium phosphate, bioglasses, calcium sulfate, etc.) tyrosine-derived polycarbonate poly (DTE-co-DT carbonate), in which the pendant group via the tyrosine—an amino acid—is either an ethyl ester (DTE) or free carboxylate (DT) or combinations thereof.

In some embodiments, the matrix comprises collagen. Exemplary collagens include human or non-human (bovine, ovine, and/or porcine), as well as recombinant collagen or combinations thereof. Examples of suitable collagen include, but are not limited to, human collagen type I, human collagen type II, human collagen type III, human collagen type IV, human collagen type V, human collagen type VI, human collagen type VII, human collagen type VIII, human collagen type IX, human collagen type X, human collagen type XI, human collagen type XII, human collagen type XIII, human collagen type XIV, human collagen type XV, human collagen type XVI, human collagen type XVII, human collagen type XVIII, human collagen type XIX, human collagen type XXI, human collagen type XXII, human collagen type XXIII, human collagen type XXIV, human collagen type XXV, human collagen type XXVI, human collagen type XXVII, and human collagen type XXVIII, or combinations thereof. Collagen further may comprise hetero- and homo-trimers of any of the above-recited collagen types. In some embodiments, the collagen comprises hetero- or homo-trimers of human collagen type I, human collagen type II, human collagen type III, or combinations thereof.

In some embodiments, the matrix comprises collagen-containing biomaterials from the implant market which, when placed in a bone defect, provide scaffolding around which the patient's new bone will grow, gradually replacing the carrier matrix as the target site heals. Examples of suitable carrier matrices may include, but are not limited to, the MasterGraft® Matrix produced by Medtronic Sofamor Danek, Inc., Memphis, Tenn.; MasterGraft® Putty produced by Medtronic Sofamor Danek, Inc., Memphis, Tenn.; Absorbable Collagen Sponge ("ACS") produced by Integra LifeSciences Corporation, Plainsboro, N.J.; bovine skin collagen fibers coated with hydroxyapatite, e.g. Healos® marketed by Johnson & Johnson, USA; collagen sponges, e.g. Hemostagene® marketed by Coletica S A, France, or e.g. Helisat® marketed by Integra Life Sciences Inc., USA; and Collagraft® Bone Graft Matrix produced by Zimmer Holdings, Inc., Warsaw, Ind.

In some embodiments, the embodiments the matrix may comprise particles of bone-derived materials. The bone-derived material may include one or more of non-demineralized bone particles, demineralized bone particles, lightly demineralized bone particles, and/or deorganified bone particles.

In some embodiments, the matrix may be seeded with harvested bone cells and/or bone tissue, such as for example, cortical bone, autogenous bone, allogenic bones and/or xenogenic bone. In some embodiments, the matrix may be seeded with harvested cartilage cells and/or cartilage tissue (e.g., autogenous, allogenic, and/or xenogenic cartilage tissue). For example, before insertion into the target tissue site, the matrix can be wetted with the graft bone tissue/cells, usually with bone tissue/cells aspirated from the patient, at a ratio of about 3:1, 2:1, 1:1, 1:3 or 1:2 by volume. The bone tissue/cells are permitted to soak into the matrix provided, and the matrix may be kneaded by hand or machine, thereby obtaining a pliable consistency that may subsequently be packed into the bone defect. In some embodiments, the matrix provides a malleable, non-water soluble carrier that permits accurate placement and retention at the implantation site.

The matrix may contain an inorganic material, such as an inorganic ceramic and/or bone substitute material. Exemplary inorganic materials or bone substitute materials include but are not limited to aragonite, dahlite, calcite, amorphous calcium carbonate, vaterite, weddellite, whewellite, struvite, urate, ferrihydrate, francolite, monohydrocalcite, magnetite, goethite, dentin, calcium carbonate, calcium sulfate, calcium phosphosilicate, sodium phosphate, calcium aluminate, calcium phosphate, hydroxyapatite, alpha-tricalcium phosphate, dicalcium phosphate, β-tricalcium phosphate, tetracalcium phosphate, amorphous calcium phosphate, octacalcium phosphate, BIOGLASS™, fluoroapatite, chlorapatite, magnesium-substituted tricalcium phosphate, carbonate hydroxyapatite, substituted forms of hydroxyapatite (e.g., hydroxyapatite derived from bone may be substituted with other ions such as fluoride, chloride, magnesium sodium, potassium, etc.), or combinations or derivatives thereof.

In some embodiments, tissue will infiltrate the matrix to a degree of about at least 50 percent within about 1 month to about 6 months after implantation of the matrix. In some embodiments, about 75 percent of the matrix will be infiltrated by tissue within about 2-3 months after implantation of the matrix. In some embodiments, the matrix will be substantially, e.g., about 90 percent or more, submerged in or enveloped by tissue within about 6 months after implantation of the matrix. In some embodiments, the matrix will be completely submerged in or enveloped by tissue within about 9-12 months after implantation.

In some embodiments, the matrix has a thickness of from 0.25 mm to 5 mm, or from about 0.4 mm to about 2 mm, or 0.4 mm to about 1 mm. Clearly, different bone defects (e.g., osteochondral defects) may require different matrix thicknesses.

In some embodiments, the matrix has a density of between about 1.6 g/cm$^3$, and about 0.05 g/cm$^3$. In some embodiments, the matrix has a density of between about 1.1 g/cm$^3$, and about 0.07 g/cm$^3$. For example, the density may be less than about 1 g/cm$^3$, less than about 0.7 g/cm$^3$, less than about 0.6 g/cm$^3$, less than about 0.5 g/cm$^3$, less than about 0.4 g/cm$^3$, less than about 0.3 g/cm$^3$, less than about 0.2 g/cm$^3$, or less than about 0.1 g/cm$^3$.

The shape of the matrix may be tailored to the site at which it is to be situated. For example, it may be in the shape of a morsel, a plug, a pin, a peg, a cylinder, a block, a wedge, a sheet, etc.

In some embodiments, the diameter or diagonal of the matrix can range from 1 mm to 50 mm. In some embodiments, the diameter or diagonal of the matrix can range from 1 mm to 30 mm, or 5 mm to 10 mm which is small enough to fit through an endoscopic cannula, but large enough to minimize the number of matrices needed to fill a large the bone defect (e.g., osteochondral defect).

In some embodiments, the matrix may be made by injection molding, compression molding, blow molding, thermoforming, die pressing, slip casting, electrochemical machining, laser cutting, water-jet machining, electrophoretic deposition, powder injection molding, sand casting, shell mold casting, lost tissue scaffold casting, plaster-mold casting, ceramic-mold casting, investment casting, vacuum casting, permanent-mold casting, slush casting, pressure casting, die casting, centrifugal casting, squeeze casting, rolling, forging, swaging, extrusion, shearing, spinning, powder metallurgy compaction or combinations thereof.

In some embodiments, a therapeutic agent (including one or more growth factors) may be disposed on or in the matrix by hand, electrospraying, ionization spraying or impregnating, vibratory dispersion (including sonication), nozzle spraying, compressed-air-assisted spraying, brushing and/or pouring. For example, a growth factor such as rhBMP-2 may be disposed on or in the matrix.

In some embodiments, the matrix may comprise sterile and/or preservative free material.

The matrix can be implanted by hand or machine in procedures such as for example, laparoscopic, arthroscopic, neuroendoscopic, endoscopic, rectoscopic procedures or the like.

In one embodiment, the isolated osteoinductive agents include one or more members of the family of Bone Morphogenic Proteins ("BMPs"). These can be disposed on the matrix. BMPs are a class of proteins thought to have osteoinductive or growth-promoting activities on endogenous bone tissue, or function as pro-collagen precursors. Known members of the BMP family include, but are not limited to, BMP-1, BMP-2, BMP-3, BMP-4, BMP-5, BMP-6, BMP-7, BMP-8, BMP-9, BMP-10, BMP-11, BMP-12, BMP-13, BMP-15, BMP-16, BMP-17, BMP-18 as well as polynucleotides or polypeptides thereof, as well as mature polypeptides or polynucleotides encoding the same.

BMPs utilized as osteoinductive agents comprise one or more of BMP-1; BMP-2; BMP-3; BMP-4; BMP-5; BMP-6; BMP-7; BMP-8; BMP-9; BMP-10; BMP-11; BMP-12; BMP-13; BMP-15; BMP-16; BMP-17; or BMP-18; as well as any combination of one or more of these BMPs, including full length BMPs or fragments thereof, or combinations thereof, either as polypeptides or polynucleotides encoding the polypeptide fragments of all of the recited BMPs. The isolated BMP osteoinductive agents may be administered as polynucleotides, polypeptides, full length proteins or combinations thereof.

In some embodiments, the BMP is rhBMP-2 and is contained in one or more matrices in an amount of from 1 to 2 mg per cubic centimeter of the biodegradable matrix. In some embodiments, the amount of rhBMP-2 morphogenic protein is from 2.0 to 2.5 mg per cubic centimeter (cc) of the biodegradable matrix.

In some embodiments, the BMP and/or NBD peptide is supplied in a liquid carrier (e.g., an aqueous buffered solution). Exemplary aqueous buffered solutions include, but are not limited to, TE, HEPES (2-[4-(2-hydroxyethyl)-1-piperazinyl]ethanesulfonic acid), MES (2-morpholinoethanesulfonic acid), sodium acetate buffer, sodium citrate buffer, sodium phosphate buffer, a Tris buffer (e.g., Tris-HCL), phosphate buffered saline (PBS), sodium phosphate, potassium phosphate, sodium chloride, potassium chloride, glycerol, calcium chloride or a combination thereof. In various embodiments, the buffer concentration can be from about 1 mM to 100 mM.

In some embodiments, the BMP-2 is provided in a vehicle (including a buffer) containing sucrose, glycine, L-glutamicacid, sodium chloride, and/or polysorbate 80.

Methods of Treatment

As described above, illustrative target tissue sites (e.g., bone repair or bone defect sites) that can be treated with compositions of the disclosure include, for instance, those resulting from injury, defects brought about during the course of surgery, infection, malignancy or developmental malformation. The composition can be used in a wide variety of orthopedic, periodontal, neurosurgical and oral and maxillofacial surgical procedures including, but not limited to the repair of simple and compound fractures and non-unions; external and internal fixations; joint reconstructions such as arthrodesis; general arthroplasty; cup arthroplasty of the hip; femoral and humeral head replacement; femoral head surface replacement and total joint replacement; repairs of the vertebral column including spinal fusion and internal fixation; tumor surgery, e.g., deficit filing; discectomy; laminectomy; excision of spinal cord tumors;

anterior cervical and thoracic operations; repairs of spinal injuries; scoliosis, lordosis and kyphosis treatments; intermaxillary fixation of fractures; mentoplasty; temporomandibular joint replacement; alveolar ridge augmentation and reconstruction; inlay osteoimplants; implant placement and revision; sinus lifts; cosmetic enhancement; etc. Specific bones which can be repaired or replaced with the bone material include, but are not limited to the ethmoid; frontal; nasal; occipital; parietal; temporal; mandible; maxilla; zygomatic; cervical vertebra; thoracic vertebra; lumbar vertebra; sacrum; rib; sternum; clavicle; scapula; humerus; radius; ulna; carpal bones; metacarpal bones; phalanges; ilium; ischium; pubis; femur; tibia; fibula; patella; calcaneus; tarsal and metatarsal bones.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

Having now generally described the invention, the same may be more readily understood through the following reference to the following examples, which are provided by way of illustration and are not intended to limit the present invention unless specified.

EXAMPLES

Example 1

Section C: ERP Study Protocol
Background
Abstract

Recombinant human bone morphogenic protein-2 (rhBMP-2) has been successfully used to enhance bone formation in spine surgery. However, side effects, such as formation of rhBMP-2-induced soft-tissue edema, have been reported. NFκB is a central regulator of immune response through regulation of genes encoding pro-inflammatory cytokines, such as TNF-α and Il-1β. NEMO binding domain peptide (NBD) is a non-toxic agent that allows for the selective inhibition of NFκB activation without affecting NFκB's basal activity. Therefore, NBD is an interesting candidate to reduce rhBMP-2-related soft-tissue inflammation.

In this proposed study we hypothesize that addition of NBD will reduce soft-tissue inflammation induced by an intramuscular implantation of rhBMP-2-loaded absorbable collagen sponges (ACS) in rats. The aims of this project are, therefore, to identify an efficient dose of NBD that results in a reduction of rhBMP-2-induced inflammation in a rat model of soft-tissue inflammation, and to demonstrate diminished DNA binding of NFκB as well as reduced levels of expression of NFκB-regulated genes in NPB/BMP-2/ACS-treated soft tissues compared to controls.

The reduction of inflammatory processes in response to NBD will be evaluated in a well-established rat animal model of rhBMP-2-induced edema. ACS implants containing high dose rhBMP-2 and different doses of NBD will be compared to ACS/BMP-2 (positive control), as well as ACS/PBS buffer, ACS/NBD and incision only (negative controls). Constructs will be implanted into intramuscular fusion beds of rats and evaluated two days after surgery. Edema volume will be assessed using MRI. Cell activity in implant-surrounding muscle tissue will be performed using a hematoxylin/eosin staining. The NFκB DNA binding activity and expression of the NFκB-regulated genes, Il-1β, Il-6, Il-18, TNF-α, CCL-2 (MCP-1) and CCL-3 (MIP-1α), in treated soft tissues and controls will be analyzed in terms of EMSA and quantitative RT-PCR.

At the end of this study, the efficacy and appropriate dose of NBD to decrease rhBMP-2-induced soft-tissue edema and reduce the activation of the NFκB and transcription NFκB-regulated genes in a rat model will be presented. The results of this study might provide the basis to develop new therapeutic approaches using a combinatory administration of NBD and rhBMP-2 to reduce the potential of rhBMP-2 induced soft-tissue inflammation in spinal fusion procedures.

Clinical Problem

Recombinant human BMP-2 (rhBMP-2) is known to contribute to rapid and effective spinal fusion (Hsu and Wang 2001). The use of this protein for anterior lumbar interbody fusion has been approved by the U.S. Food and Drug Administration in 2002. However, several adverse events have been reported, including rhBMP-2 associated soft tissue swelling and inflammation (Perri, Cooper et al. 2007; Carragee, Hurwitz et al. 2011). Risk factors for adverse events include high doses of rhBMP-2 and off-label use in the cervical spine (Shields, Raque et al. 2006; Perri Cooper et al. 2007) (Smucker, Rhee et al. 2006). A cytokine-mediated inflammatory reaction after posterior cervical fusion in presence of rhBMP-2 has been described, including the pro-inflammatory proteins interleukin-6 (Il-6), tumor necrosis factor-α (TNF-α) and chemokine (C-C motif) ligands, such as CCL-2 and CCL-3 (Robin, Chaput et al. 2010; Hsu, Polavarapu et al. 2013). To study the inflammatory responses to rhBMP-2 in more detail, rat animal models of soft-tissue inflammation were developed (Lee, Taghavi et al. 2011; Bae, Strenge et al. 2012). These studies demonstrated a formation of soft tissue edema in response to intramuscularly implanted high dose rhBMP-2 on day 2 (Lee, Taghavi et al. 2011; Bae, Strenge et al. 2012). Furthermore, an increased expression of pro-inflammatory cytokines has been demonstrated, including TNF-α and Il-6 (Lee, Taghavi et al. 2011).

The Role of NFκB in Inflammation

The inducible transcription factor NFκB plays a crucial role in the inflammatory response. Activation of NFκB has been shown to be important in many inflammatory diseases including rheumatoid arthritis and intervertebral disc disease (Baldwin 2001; Wuertz, Vo et al. 2012). It is induced by a variety of molecules, including TNF-α and Il-1β (Wang, Xu et al. 2011). Activation of NFκB results in the transcription of target genes, including the cytokines TNF-α, IL-1β, Il-6 and 11-18, which can further increase the inflammatory response (Pahl 1999; Gracie, Robertson et al. 2003; di Meglio, Ianaro et al. 2005). Furthermore, CC-motif ligands such as CCL-2 (MCP-1) and CCL-3 (MIP-1α) are prominent target genes of the NFκB signaling pathway (Hoesel and Schmid 2013). An increased expression of these chemokines has been shown to attract pro-inflammatory cells such as macrophases, which further increase the inflammatory response (Risbud and Shapiro 2014).

The most prevalent form of NFκB is a heterodimer consisting of the p50 and p65 subunits. In unstimulated cells, NFκB proteins are localized in the cytoplasm and bound to IκB proteins that marks their nuclear localization signals. Binding of TNF-α or Il-1 to the cell surface results in the phosphorylation of IκB proteins, which leads to the degradation of IκB in the proteasome and thereby releases NFκB, which can translocate to the nucleus. The phosphorylation of IκB is mediated by a specific IκB kinase (IKK), which is a complex of two catalytic subunits IKK alpha and beta and a regulatory subunit named NFκB essential modulator (NEMO) (di Meglio, lanaro et al. 2005).

Treatment of Inflammation by NFκB Suppression

Corticosteroids are known to reduce soft tissue inflammation in spinal procedures, but have been associated with side effects, especially when used in higher doses (Matsumoto, Tamaki et al. 200 I; Kim and Brown 2011; Lee, Kim et al. 2011; Tan, Montgomery et al. 2013).

NBD peptide has been shown to block pro-inflammatory cytokine-induced NFκB activation without affecting the basal activity of IKK in an in vivo model (di Meglio, lanaro et al. 2005). Furthermore, continuous administration of NBD was demonstrated to prevent inflammatory bone destruction in vivo without showing signs of toxicity (Jimi, Aoki et al. 2004). Local treatment of NBD has been shown to have anti-inflammatory effects on human rheumatoid arthritis and has been shown to reduce osteoclastogenesis and bone erosion in inflammatory arthritis (Dai, Hirayama et al. 2004; Tas, Vervoordeldonk et al. 2006). Moreover, NBD has been shown to significantly inhibit carrageenan-induced edema formation and cellular inflammation in mouse paws (di Meglio, lanaro et al. 2005). However, to our knowledge, there is no information on the potential of NBD in rhBMP-2 induced in edema so far.

Study Purpose/Objectives

We hypothesize that inhibition of NFκB activation using the NEMO binding domain peptide (NBD) results in a reduction of rhBMP-2-induced inflammation in a rat model of soft-tissue inflammation.

The aims of this project arc therefore to identify an efficient dose of NBD that results in a reduction of rhBMP-2-induccd edema in a rat model of soft-tissue inflammation and to demonstrate a reduced NFκB DNA binding activity and reduced expression of NFκB-regulated genes in NBD treated soft tissues compared to controls.

Study Design

In previous research studies of our group, inflammatory responses to increasing doses of rhBMP-2 on an ACS sponge were tested in rats; a significant formation of soft tissue edema in response to 129 µg rhBMP-2 was demonstrated on day 2 (Bae, Strenge et al. 2012). Based on these results, 129 µg rhBMP-2 will be used to induce a robust inflammatory response in the proposed study. Furthermore, a significantly higher edema volume has been demonstrated on day 2 postoperatively compared to day 7 (Bae, Strenge et al. 2012). Therefore, this proposed study will focus on tissue evaluation on day 2. Since an administration of 100 µg and 500 µg NBD has been shown to ameliorate paw edema in mice (di Meglio, lanaro et al. 2005), these concentrations are included in the study design.

Institutional animal care and use committee (IACOC) approval will be acquired upon notification by the ERP Program Administrator. Forty-five 8-wcek-old male Lewis rats will be divided randomly into 7 equal groups and treated according to IACOC protocol for experimental procedures. ACS will be loaded with 129 µg rhBMP-2 and intramuscularly implanted to induce a strong inflammatory response in rat soft tissue (Table I, group I). To evaluate the reduction of soft tissue inflammation in response to NBD peptide, ACS containing 129 µg rhBMP-2 will be implanted into paraspinal muscle tissue in presence and absence of NBD. One hundred NBD/ACS/BMP-2 (group II) and 500 µg NBDI-ACS/BMP-2 (group III) will be administered and compared against the positive control ACSIBMP-2 (group I), as well as the negative controls, 100 µg NBD/ACS (group IV), 500 µg NBD/ACS (group V), PBS/ACS (group VI) and incision only (group VII). MRI will be used to assess edema volume. To detect inflammation in histological analyses, a hematoxylin/eosin staining will be performed. Furthermore, EMSA and quantitative RT-PCR will be conducted to evaluate the activity of NFκB and NFκB-regulated genes in NBD-treated soft tissues and controls.

Milestones

The primary milestone to achieve is to demonstrate that application of NBD results in a reduction of rhBMP-2-induced formation of edema in a rat model of soft-tissue inflammation by performing surgery on 63 animals and performing Mill and histological analyses.

Secondary milestones to achieve is to demonstrate reduced levels of the NFκB DNA binding activity and expression of NFκB-regulated proteins compared to controls after treatment of soft tissues with NBD by performing EMSA and qPCR analyses.

Study Product or Therapy

NBD is currently not therapeutically used in humans. However, different in vitro and in vivo assays indicate that NBD might be a potential candidate to reduce rhBMP-2-induced soft-tissue inflammation. A potential indication of this product is the combinatory administration of NBD with rhBMP-2 to reduce the occurrence of rhBMP-2 induced soft-tissue inflammation in spinal fusion procedures.

Study Procedures, Materials and Methods

Animal Surgery

Rats will be anesthetized using 2.5% isoflurane inhalation in oxygen. A 25 mm posterior longitudinal incision will be bilaterally made and ASCs will be implanted into 10 mm×10 mm pockets in the paraspinal muscle tissue.

Absorbable collagen sponges will be loaded with 129 µg rhBMP-2 and intramuscularly implanted to induce a strong inflammatory response in rat soft tissue (Table I, group I). To evaluate the reduction of soft tissue inflammation in response to NBD peptide, the absorbable collagen sponge with high dose rhBMP-2 will be supplemented with 100 µg NBD and 500 NBD (Table I, groups II and III). ACS/NBD (100 µg), ACS/NBD (500 PBS/ACS and incision only will serve as negative controls (Table 1, groups IV, V, VI and VII). After implantation, muscles and skin will be closed with non-absorbable sutures.

TABLE I

Testing of the effect of NBD peptide for a reduction of soft tissue inflammation on day 2 postoperatively. Shown are the numbers of animals that will be used for each experiment (n = 9 per experimental group as MRI is performed on same animals as other measures).

| Method Of Evaluation | I BMP-2 ACS | II BMP-2 + ACS + NBD (100111) | III BMP-2 + ACS + NBD (500 µg) | IV control (ACS + NB (100 µg)) | V control (ACS + NBD (500 µg)) | VI control (PBS + ACS) | VII control (incision only) |
|---|---|---|---|---|---|---|---|
| MRI | 9 | 9 | 9 | 9 | 9 | 9 | 9 |
| Histology | 3 | 3 | 3 | 3 | 3 | 3 | 3 |
| RT-PCR | 3 | 3 | 3 | J | 3 | 3 | 3 |
| EMSA | 3 | 3 | 3 | 3 | 3 | 3 | 3 |

MRI Evaluation

Magnetic resonance imaging (MM) will be used to asses soft-tissue edema volume as an index of inflammation in the presence and absence of NBD in groups I-VII on day 2. A small animal magnetic resonance imaging scanner, Bruker BioSpec 9.4T (94/20) with Avance III electronics 9.4T will be employed with support of the Research Imaging Core, Cedars-Sinai Medical Center. The imager is equipped with two bar channel array coils, a 1H 65 mm quadrature coil, 1H 35 mm quadrature coil, 1H 35 mm quadrature coil, small 1H surface coil, linear 1H transmission coil and a variety of in-house custom 1H and X nuclei coils. Axial sequences with a slice thickness of 1 mm will be obtained throughout the paraspinal tissues. The volume of inflammatory edema surrounding the intramuscular implants will be measured using MIPAV computer imaging software (Medical Image Processing. Analysis, and Visualization, NIH, Bethesda, Md.). A grayscale auto-thresholding function will be used to trace the area of inflammatory edema per slice (mm2) and multiplied by slice number and thickness lo give the total volume. Data will be determined from nine rats.

Histology

A hematoxin-eosin staining will be performed to qualitatively analyze the cellular activity of the inflammatory zones surrounding the implants in presence and absence of NBD (groups I-VII), as described earlier (Bae, Strenge et al. 2012). Therefore, rats will be sacrificed on day 2 postoperatively and soft tissue including muscle, and implants will be collected and fixed in 10% formalin. Dehydrated specimens will be embedded in paraffin and cut into 5 µm sections. Data will be determined from three rats.

Preparation of Tissue Nuclear Extracts and EMSA

To demonstrate a reduced NFκB DNA binding activity in soft-tissue in presence NBD compared to controls, an Electrophoretic Mobility-Shift Assay (EMSA) Kit, with SYPRO® Green & SYPRO® Ruby EMSA stains (Life Technologies, USA) will be performed according to manufacturer's instructions. Tissue nuclear extracts will be obtained according to Di Meglio et al. (di Meglio, lanaro et al. 2005). Briefly, soft tissue including muscle and implants will be frozen in liquid nitrogen, immediately suspended in an ice-cold hypotonic lysis buffer, and homogenized using a tissue homogenizer. The homogenates will be chilled on ice, then vigorously shaken in the presence of 5% Nonidet P40 and again incubated on ice. The nuclear fraction will be precipitated by centrifugation at 1,500 g and the supernatant removed. The nuclear pellet will be resuspended in high salt extraction buffer and centrifuged for 15 min at 13,000 g. Protein concentration will be determined in terms of a Bradford assay. Samples will be aliquoted and stored at −80° C. until assay performance. Data will be determined from three rats.

RNA Isolation and Quantitative RT-PCR

Total RNA will be isolated from treated soft tissue using TR1zol Reagent (lnvitrogen, Karlsbad, Calif.) and subsequent homogenization, as described earlier by Schmidt-Bleek et al. (Schmidt-Bleek, Schell et al. 2012). Briefly, chloroform will be added, mixed and incubated. After centrifugation the clear upper phase will be collected, and 2-propanol added (1:2). After mixing and centrifugation the pellet will be resuspended in 75% ethanol. Following centrifugation, the pellet will be dried at 37° C. and resuspended in DEPC water at 50° C. After cooling. DNase-Mix (Quiagen, Hilden, Germany) will be added. Then, TR1zol®Reagent will be added and the procedure repeated until the re-suspension of the pellet in RNase-free water at 50° C. The quality and quantity of the RNA will be determined by spectrophotometry. Samples will be aliquoted and stored at −80° C. until assay performance. For qPCR., the Bio-Rad CFX96 Touch™ Real-Time PCR Detection System (Bio-Rad, Hercules, Calif.) will be employed. RNA will be transcribed in cDNA and levels of IL1-β, IL-6, IL-18, TNF-α, CCL-2 and CCL-3 will be detected in terms of commercially available TaqMan® Expression Assays according to manufacturer's instructions (LifeTechnologies, USA). Expression levels of mRNA will be normalized to β-actin. For data analysis, the 2-ΔΔCq (Livak) Method will be used. Data will be determined from three rats.

Example 2

Significance

Recombinant human bone morphogenic protein-2 (rhBMP-2) has been successfully used to enhance bone formation in spine surgery. However, side effects, such as formation of rhBMP-2-induced soft-tissue edema, have been reported. NFκB is a central regulator of immune response through regulation of genes encoding pro-inflammatory cytokines, such as TNF-α and Il-1β. NEMO binding domain peptide (NBD) is a non-toxic agent that allows for the selective inhibition of NFκB activation without affecting NFκB's basal activity. Therefore, NBD is an interesting candidate to reduce rhBMP-2-related soft-tissue inflammation.

We recently demonstrated that addition of NBD to intramuscularly implanted rhBMP-2-loaded absorbable collagen sponges (ACS) reduces rhBMP-2 induced soft-tissue inflammation in rat. This reduction has been demonstrated in terms of magnetic resonance imaging showing a reduced amount of edema at the site of NBD- and BMP-2-loaded ACS implant compared to BMP-2-loaded ACS. Furthermore, we demonstrated that RNA levels of the pro-inflammatory cytokines IL1β, IL6 and IL18 and inflammatory cell-associated chemokines CCL 2 and CCL 3 are reduced in BMP-2- and NBD-loaded ACS compared to BMP-2-loaded ACS. However, it is still unknown, whether NBD affects BMP-2 induced bone formation.

The aim of this study was therefore to demonstrate that amounts of NBD that efficiently reduce BMP-2-induced soft tissue inflammation do not interfere with BMP-2-induced bone formation in a rat spine fusion model.

Sixteen male adult (220 to 260 g) Sprague Dawley rats were utilized to compare BMP-2 mediated spine fusion in presence and absence of NBD. Based on a study by Bae, H W et al in 2013 (J Bone Joint Surg Am), a total dose of 30 μg rhBMP-2/side/rat results in 100% spine fusion. Therefore, this concentration of BMP-2 was employed. In detail, eight rats underwent single-level posterolateral fusion in the lumber spine using BMP-2 (total dose of 30 μg/side/rat) and NBD (100 g) loaded ACS and eight rats served as positive controls (30 μg/side/rat BMP-2-loaded ACS, no NBD). Rat spines were allowed to heal and consolidate for 12 weeks. Radiographical fusion was determined via high-resolution radiographs obtained at monthly intervals postoperatively. After 12 weeks, ex vivo micro-computed tomography was performed on explanted spines to determine the structural properties of the fusion mass. For functional assessment of spinal fusion, manual palpation was performed. Finally, histological evaluation of spine fusion was performed in terms of Masson-trichrome staining (Table 1).

TABLE 1

Experimental groups

| Method of evaluation | I ACS + BMP-2 | II ACS + BMP-2 + NBD (100 μg) |
|---|---|---|
| X-ray | 8 | 8 |
| Micro-CT | 8 | 8 |
| Manual palpation | 6 | 6 |
| Histology | 2 | 2 |
| Total amount of animals | 8 | 8 |

Experimental Details

Fusion Procedure

The posterolateral intertransverse process fusion surgical procedure is described briefly. With the rat under 2% to 2.5% inhaled isoflurane anesthesia, a posterior midline longitudinal incision was made at the lumbar spine. Dissection was performed to expose the transverse processes of L4 and L5. The transverse processes were decorticated with a high-speed burr until punctate bleeding, whereas the lamina and facet joints were left intact. No internal fixation was used. The surgical site was irrigated with antibiotic Ringer solution and packed with gauze until the implants are prepared. The surgeon was blinded to the experimental assignment until after surgical preparation.

A 7 to 10-mm space exists between the transverse processes of L4 and L5. The loaded ACS implants were placed bilaterally in the paraspinal muscle bed, between and touching the transverse processes of L4 and L5. The fascia and skin were closed with 3-0 absorbable suture and 3-0 nylon suture, respectively. The rats were housed in separate cages, allowed to eat and drink ad libitum, and managed with subcutaneous injections of buprenorphine (0.5 mg/kg) for the control of perioperative and postoperative pain. The condition of the rats was monitored daily. The rats were sacrificed at twelve weeks after surgery.

High Resolution Radiographs and Micro-Computed Tomographic Scans

Radiographical fusion was determined via high-resolution radiographs (LX-60, Faxitron X-Ray, LLC Lincolnshire, Ill.) obtained at monthly intervals postoperatively under inhalation anesthesia. Radiographs were characterized for radiographical fusion defined as density showing any continuous bridging of the TPs bilaterally "fused" versus "not fused." Ex vivo micro-computed tomography (vivaCT 40, Scanco USA Inc., Wayne, Pa.) was performed on explanted spines to determine the structural properties of the fusion mass. The L4-L5 region including the upper and lower spinal segment was contoured and segmented from soft tissue using a binary thresholding procedure. The Researcher was blinded to the experimental condition of the site. Direct 3-dimensional morphometry was used to determine (a) volume of mineralized bone tissue (BV), (b) connectivity density (Conn.D.), (c) bone mineral density (BMD), (d) trabecular number (Tb.N.), (e) trabecular thickness (Tb.Th.) and (f) trabecular spacing (Tb.Sp.).

Manual Palpation Fusion

Fusion was determined via manual palpation of segments by two independent observers. Any motion that was detected between the L4 and L5 segment, including the transverse process or vertebral bodies, was considered to indicate a fusion failure. Each side was tested separately; the observation of no motion on both the right and left sides indicated a successful fusion.

Histology

Lumbar vertebral specimens were fixed in 10% neutral buffered formalin, the lumbar spine decalcified using a 15% EDTA solution, embedded in paraffin, sectioned in the sagittal plane and stained with Masson-trichrome.

Results

NBD Supplementation Stimulates rhBMP-2 Induced Spine Fusion

Figures 1A, 1B, 1C:
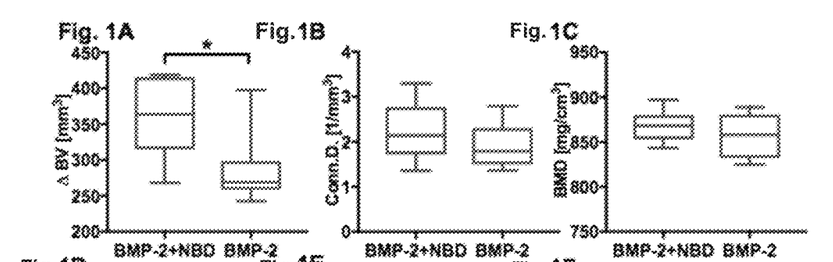
FIGS. 1A, 1B, 1C, 1D, 1E, 1F, 1G, and 1H illustrate bone volume being increased and trabecular spacing decreased in the presence of NBD.
Figures 1D, 1E, 1F:
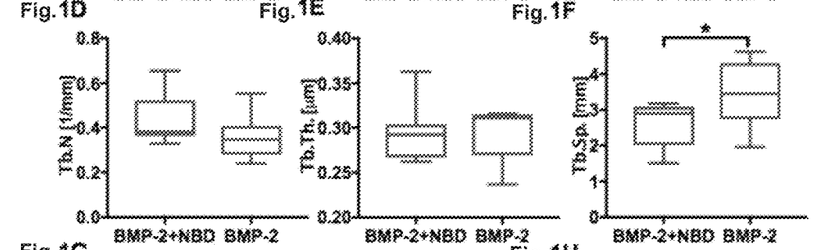
Figure 1G:
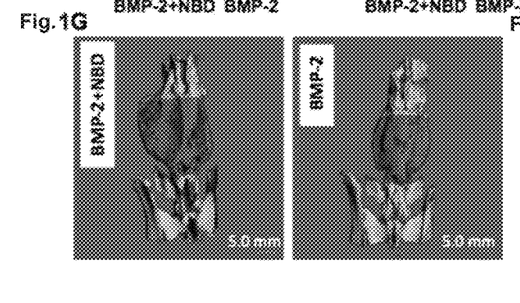
Figure 1H:
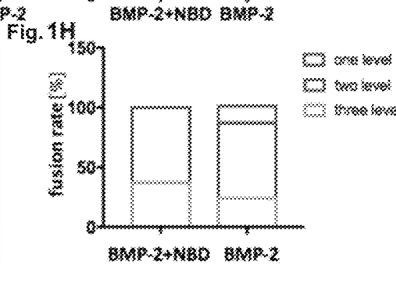

Micro CT analyses of explanted spines of experimental groups I(BMP-2+NBD) and group II(BMP-2) were performed 12 weeks after surgery, as fusion could be determined radiographically after this time (see supplemental data). CT data evaluation showed a significant increase in the Δ bone volume ((bone volume at week 12)–(pre-surgical bone volume)) and a decreased trabecular spacing of group I compared to group II (median Δ BV: group I: 363.9, min: 267.9.0, max: 418.7; group II: 269.2, min: 242.5, max: 397.9, p≤0.05; median Tb.Sp: group I: 2.9, min:1.5, max: 3.1; group II: 3.5, min: 2.0, max: 4.6, p≤0.05) (FIGS. 1A, F and G). No differences were detected in connectivity density, bone mineral density, trabecular number and trabecular thickness. Manual palpation of freshly harvested spine explants showed 100% fusion in both experimental groups, with more levels fused in the BMP+NBD group (FIG. 1H).

FIG. 1 A-H shows how one volume is increased and trabecular spacing is decreased in the presence of NBD. FIG. 1 A-F shows the differences between rhBMP-2+NBD vs. NBD groups in the bone quality at the contoured region of L4-5 and adjacent levels. Data were obtained on the bone volume [(BV) week 12 post-surgery-pre-surgery)], connectivity density (Conn.D.), bone mineral density (BMD), trabecular number (Tb.N), trabecular thickness (Tb.Th.) and trabecular spacing (Tb.Sp.). FIG. 1G is a representative 3D image of the contoured spine region of rhBMP-2+NBD vs. NBD groups. In FIG. 1H manual palpation shows 100% fusion in both experimental groups, with more levels fused in the rhBMP-2+NBD group.

Figure 2:
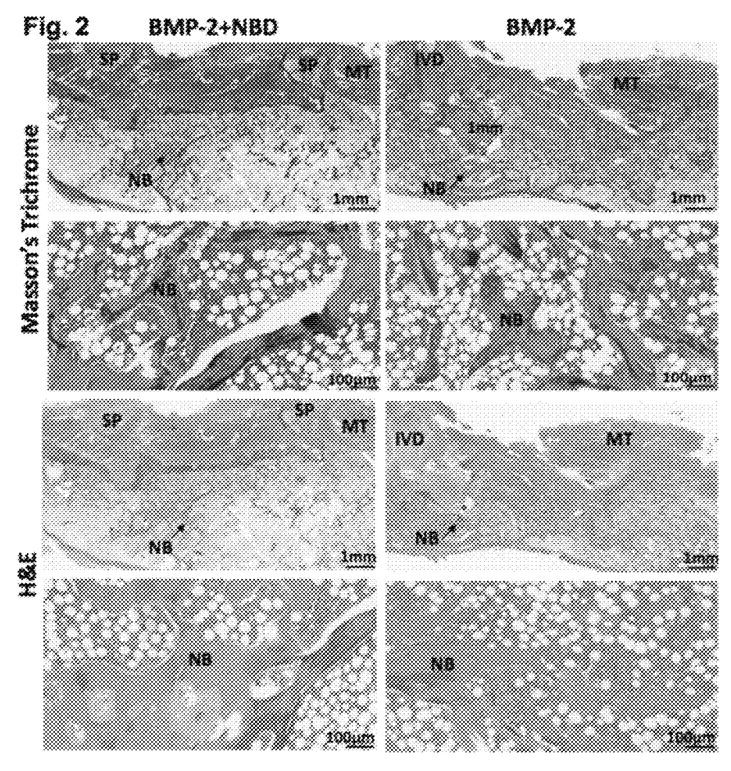
FIG. 2 illustrates representative images of fusion masses where BMP-2 on a matrix alone was administered compared to the combination BMP-2 and NBD on a matrix.
Figure 3:
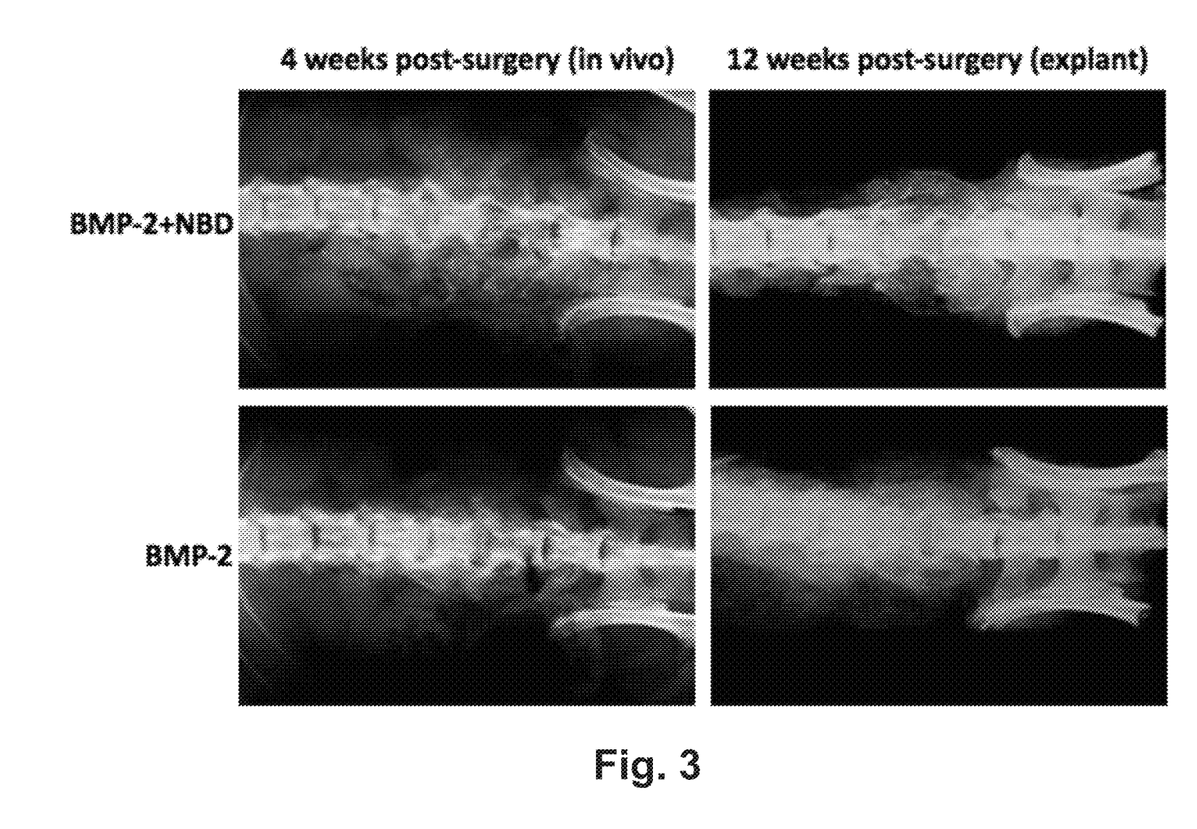
FIG. 3 illustrates Faxitron images of bone taken at weeks 4 and week 12 post-surgery.

Qualitative analysis of histological sections of newly formed bone between the spinal processes L4-5 did not indicate any differences in bone quality (FIG. 2). FIG. 2. Representative images of fusion masses. Masson's trichrome and H&E staining did not show any differences in new bone formation between rhBMP-2+NBD vs. BMP-2 groups. Low and high magnification images are shown. MT: muscle tissue; NB: new bone.

Discussion

Addition of NBD to rhBMP-2/ACS sponges, implanted into the lumbar intertransverse space, resulted in a higher bone volume and reduced trabecular spacing, and more fused levels compared to rhBMP-2/ACS sponges. Structural properties of bone tissue were similar between the experimental groups. The spinal fusion procedure was performed with a regular rhBMP-2 dose that has been shown in a prior study of our group to result in a 100% spine fusion rate in rats without showing evidence of complications [1].

Therefore, it is likely that the positive effect of NBD on bone formation is not (only) a result of attenuation of rhBMP-2 induced inflammation. Addition of NBD to rhBMP-2/ASC sponges may modulate the bone metabolism via cross talk between NF-κB and BMP signaling pathways. In line with this, a study showed that inhibition of IKK/NF-κB in differentiated osteoblasts significantly increases trabecular bone mass and bone mineral density in young mice and maintains bone formation, thereby preventing osteoporotic bone loss in adult mice [2]. Both, the canonical Smad-dependent and non-canonical BMP signaling pathway have been shown to cross-talk with the NF-κB pathway [3, 4]. For example, a regulation NF-κB by the non-canonical BMP pathway has been shown to signal via the XIAO-Tak1-Tab1 complex in endothelial cells and mouse embryonic fibroblasts (MEFs) [4-6]. A direct or indirect interaction between NF-κB and Smad signaling has been demonstrated in several studies [2, 3, 7]. For example, TNF-α has been shown to suppress BMP signaling by interfering with DNA binding of Smads through activation of NF-κB p65 in mouse embryonic fibroblasts [3]. Moreover, a recent study showed an inhibition of BMP-2 induced bone formation by the p65 subunit of NF-κB via an interaction with Smad4 [7].

Taken together, based on our results and other research on the cross-talk between NF-κB and BMP signaling pathways in bone and spine conditions, we propose that NBD may not only reduce rhBMP-2 induced inflammation and the likelihood of edema formation, but also stimulates bone formation by modulating bone metabolism. Due to the low toxicity of NBD, as shown in a phase I clinical trial in dogs[8], the concept of addition of NBD to rhBMP-2/collagen sponges for clinical use might be attractive. NBD may not only reduce the risk of inflammation, but also allow for a dose reduction of rhBMP-2. However, further research is needed to elucidate the interplay between NBD, BMP and NF-κB signaling in more detail and to demonstrate the efficacy of this peptide in larger animal models of musculoskeletal and spinal regeneration.

REFERENCES

1. Bae, H. W., et al., *Bone marrow enhances the performance of rhBMP-2 in spinal fusion: a rodent model*. J Bone Joint Surg Am, 2013. 95(4): p. 338-47.
2. Chang, J., et al., *Inhibition of osteoblastic bone formation by nuclear factor-kappaB*. Nat Med, 2009. 15(6): p. 682-9.
3. Yamazaki, M., et al., *Tumor necrosis factor alpha represses bone morphogenetic protein (BMP) signaling by interfering with the DNA binding of Smads through the activation of NF-kappaB*. J Biol Chem, 2009. 284(51): p. 35987-95.
4. Matluk, N., et al., *A role for NRAGE in NF-kappaB activation through the non-canonical BMP pathway*. BMC Biol, 2010. 8: p. 7.
5. Hofer-Warbinek, R., et al., *Activation of NF-kappa B by XIAP, the X chromosome-linked inhibitor of apoptosis, in endothelial cells involves TAK1*. J Biol Chem, 2000. 275(29): p. 22064-8.
6. Lu, M., et al., *XIAP induces NF-kappaB activation via the BIR1/TAB1 interaction and BIR1 dimerization*. Mol Cell, 2007. 26(5): p. 689-702.
7. Hirata-Tsuchiya, S., et al., *Inhibition of BMP2-induced bone formation by the p65 subunit of NF-kappaB via an interaction with Smad4*. Mol Endocrinol, 2014. 28(9): p. 1460-70.
8. Habineza Ndikuyeze, G., et al., *A phase I clinical trial of systemically delivered NEMO binding domain peptide in dogs with spontaneous activated B-cell like diffuse large B-cell lymphoma*. PLoS One, 2014. 9(5): p. e95404.

It should be understood that the forgoing relates to exemplary embodiments of the disclosure and that modifications may be made without departing from the spirit and scope of the disclosure as set forth in the following claims.

What is claimed is:

1. An osteogenic composition for implantation at or near a target tissue site beneath the skin, the osteogenic composition comprising a recombinant human bone morphogenetic protein-2 (rhBMP-2) and a NEMO binding domain peptide, wherein the NEMO binding domain peptide reduces soft tissue inflammation at or near the target tissue site, and the rhBMP-2 and the NEMO binding domain peptide are disposed on or in at least a surface of a biodegradable matrix such that the rhBMP-2 is in an amount from about 1 mg per cc of the biodegradable matrix to about 2 mg per cc of the biodegradable matrix and the biodegradable matrix has a density of between about 0.05 g/cm$^3$ and about 1.6 g/cm$^3$, wherein the rhBMP-2 and the NEMO binding domain peptide are loaded on the biodegradable matrix in a ratio of 129 μg of the rhBMP-2 to 500 μg of the NEMO binding domain peptide.

2. The osteogenic composition of claim 1, wherein the biodegradable matrix comprises porous collagen.

3. The osteogenic composition of claim 1, wherein the target tissue site is the spine.

4. The osteogenic composition of claim 1, wherein the matrix comprises a resorbable ceramic comprising hydroxyapatite.

5. An osteogenic composition for implantation at or near a target tissue site beneath the skin, the osteogenic composition comprising a recombinant human bone morphogenetic protein-2 (rhBMP-2), a NEMO binding domain peptide, and a biodegradable matrix comprising a porous collagen surface, wherein the NEMO binding domain peptide reduces soft tissue inflammation at or near the target tissue site, wherein the rhBMP-2 is in an amount from about 1 mg per cc of the biodegradable matrix to about 2 mg per cc of the biodegradable matrix and the biodegradable matrix has a density of between about 0.05 g/cm$^3$ and about 1.6 g/cm$_3$, wherein the rhBMP-2 and the NEMO binding domain peptide are loaded on the biodegradable matrix in a ratio of 129 μg of the rhBMP-2 to 500 μg of the NEMO binding domain peptide.

6. The osteogenic composition of claim 5, wherein the target tissue site is the spine.

7. A method for treating a target tissue site in a patient in need of such treatment, the method comprising implanting an osteogenic composition at or near the target tissue site beneath the skin, the osteogenic composition comprising a recombinant human bone morphogenetic protein-2 (rhBMP-2), a NEMO binding domain peptide, and a biodegradable matrix comprising a porous collagen surface, wherein the NEMO binding domain peptide reduces soft tissue inflammation at or near the target tissue, and the rhBMP-2 is in an amount from about 1 mg per cc of the matrix to about 2 mg per cc of the biodegradable matrix and the biodegradable matrix has a density of between about 0.05 g/cm$^3$ and about 1.6 g/cm$^3$, wherein the rhBMP-2 and the NEMO binding domain peptide are loaded on the biodegradable matrix in a ratio of 129 μg of the rhBMP-2 to 500 μg of the NEMO binding domain peptide.

8. The method of claim 7, wherein the target tissue site is the spine.

\* \* \* \* \*

SEQUENCE LISTING

```
<160> NUMBER OF SEQ ID NOS: 1

<210> SEQ ID NO 1
<211> LENGTH: 11
<212> TYPE: PRT
<213> ORGANISM: Homo sapiens

<400> SEQUENCE: 1

Thr Ala Leu Asp Trp Ser Trp Leu Gln Thr Glu
1               5                   10
```